(12) United States Patent
Scherzer et al.

(10) Patent No.: US 9,175,906 B2
(45) Date of Patent: Nov. 3, 2015

(54) DRUG PARTICLES FROM FREEZING ONTO A SURFACE

(75) Inventors: Brian D. Scherzer, Midland, MI (US); Jonathan C. Evans, Midland, MI (US); James E. Hitt, Midland, MI (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 609 days.

(21) Appl. No.: 10/639,361

(22) Filed: Aug. 12, 2003

(65) Prior Publication Data
US 2004/0137070 A1 Jul. 15, 2004

Related U.S. Application Data

(60) Provisional application No. 60/440,535, filed on Jan. 15, 2003.

(51) Int. Cl.
| | | |
|---|---|---|
| *A61K 9/14* | (2006.01) | |
| *F26B 17/28* | (2006.01) | |
| *A61K 9/16* | (2006.01) | |
| *A61K 9/19* | (2006.01) | |
| *A61K 31/38* | (2006.01) | |
| *F26B 5/06* | (2006.01) | |
| *A61K 6/00* | (2006.01) | |
| *A61K 9/50* | (2006.01) | |

(52) U.S. Cl.
CPC ............... *F26B 17/284* (2013.01); *A61K 9/14* (2013.01); *A61K 9/1688* (2013.01); *A61K 9/19* (2013.01); *A61K 31/38* (2013.01); *F26B 5/065* (2013.01); *A61K 6/0008* (2013.01); *A61K 9/145* (2013.01); *A61K 9/1694* (2013.01); *A61K 9/5089* (2013.01)

(58) Field of Classification Search
CPC ........ A61K 6/0008; A61K 9/14; A61K 9/145
USPC .............................. 424/489; 34/284, 285, 289
See application file for complete search history.

(56) References Cited

U.S. PATENT DOCUMENTS

| | | | | |
|---|---|---|---|---|
| 3,309,777 | A | | 3/1967 | Hutton ................................. 34/5 |
| 3,313,032 | A | | 4/1967 | Malecki .............................. 34/5 |
| 3,932,943 | A | | 1/1976 | Briggs et al. ........................ 34/5 |
| 4,745,180 | A | * | 5/1988 | Moreland et al. ............ 424/85.2 |
| 5,727,333 | A | | 3/1998 | Folan ............................... 34/285 |
| 5,780,295 | A | * | 7/1998 | Livesey et al. ............. 435/307.1 |

FOREIGN PATENT DOCUMENTS

WO     WO 02/060411 A2     8/2002

OTHER PUBLICATIONS

Williams et al., Process for Production of Nanoparticles and Microparticles by Spray Freezing into Liquid, International Application Published Under PCT, WO 02/060411 A2, Published Aug. 8, 2002. (IDS).*
Williams et al., "Process for Production of Nanoparticles and Microparticles by Spray Freezing Into Liquid", Aug. 8, 2002, International Application Published Under the PCT, WO 02/060411 A2. (Previously submitted).*
Rogers, True A, et al., "A novel particle engineering technology to enhance dissolution of poorly water soluble drugs: spray-freezing into liquid", *European Journal of Pharmaceutics and Biopharmaceuticals*, 54 (2002) pp. 271-280.
A. T. Florence, et al, "The effect of particle size reduction on digoxin crystal properties", Communications, *J. Pharm. Pharmac.*, 2 (1974), 479-180.
R. Suryanarayanan, et al., "Evaluation of tow concepts of crystallinity using calcium gluceptate as a model compound", *International Journal of Pharmaceutics*, 24 (1985), 1-17.

\* cited by examiner

*Primary Examiner* — Ali Soroush
(74) *Attorney, Agent, or Firm* — Parker Highlander PLLC

(57) ABSTRACT

The present invention is a method for preparing micron-sized or submicron-sized drug particles comprising contacting a solution comprising a poorly water soluble drug substance and at least one freezable organic solvent with a cold surface so as to freeze the solution; and removing the organic solvent. The resulting particles are also disclosed, as are several embodiments of an apparatus that can be used in performing the method of the present invention.

7 Claims, 3 Drawing Sheets

DRUG PARTICLES FROM FREEZING ONTO A SURFACE

Figure 1:
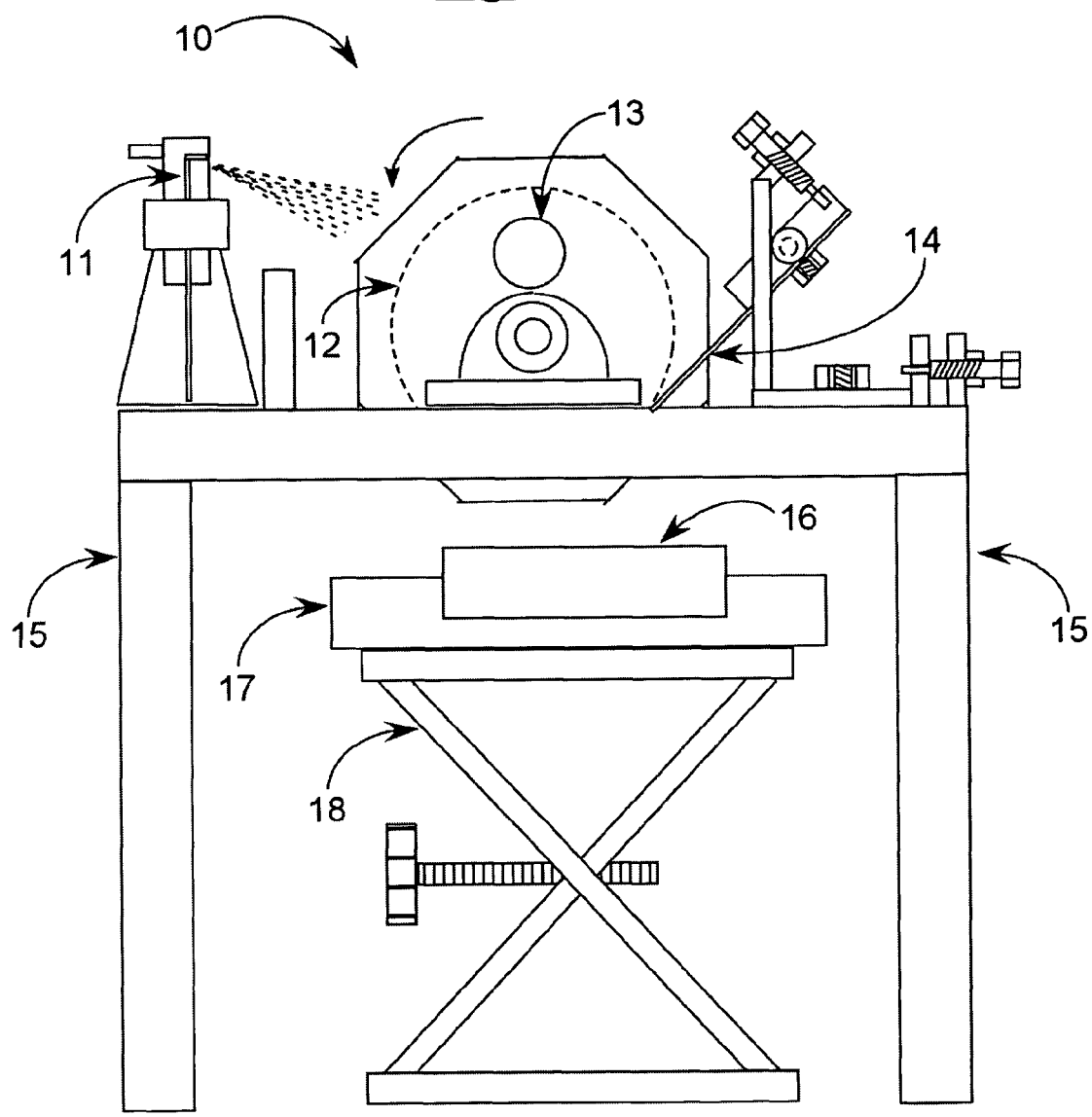

The present application claims benefit of priority to U.S. Provisional Application No. 60/440,535, filed Jan. 15, 2003.

The present invention was developed pursuant to a joint research agreement between the Dow Chemical Company and The University of Texas at Austin, a component of the University of Texas System governed by the Board of Regents of the University of Texas System.

FIELD OF THE INVENTION

The present invention relates to particles prepared by freezing onto cold solid surfaces, and in particular to the preparation of particles of poorly water soluble pharmaceutical products prepared by freezing onto cold solid surfaces.

BACKGROUND OF THE INVENTION

High bioavailability and short dissolution times are desirable attributes of a pharmaceutical end product. Bioavailability is a term meaning the degree to which a pharmaceutical product, or drug, becomes available to the target tissue after being administered to the body. Poor bioavailability is a significant problem encountered in the development of pharmaceutical compositions, particularly those containing an active ingredient that is poorly soluble in water. For example, upon oral administration poorly water soluble drugs tend to be eliminated from the gastrointestinal tract before being absorbed into the circulation.

It is known that the rate of dissolution of a particulate drug can increase with increasing surface area, i.e., decreasing particle size. Consequently, efforts have been made to control the size and size range of drug particles in pharmaceutical compositions. For example, wet milling techniques have been used, as described in U.S. Pat. No. 5,145,684. However, such wet milling techniques exhibit problems associated with contamination from the grinding media. Moreover, exposing a drug substance to excessive mechanical shear or exceedingly high temperatures can cause the drug to change or lose activity due to decomposition of the active compound, or due to recrystallization processes, i.e., formation of different crystalline polymorphs or transformation, at least in part, from the crystalline to the amorphous state, as described by Florence et al, Effect of Particle Size Reduction on Digoxin Crystal Properties, Journal of Pharmaceutics and Pharmacology, Vol. 26, No. 6, 479-480 (1974), and R. Suryanarayanan and A. G. Mitchell, Evaluation of Two Concepts of Crystallinity Using Calcium Gluceptate as a Model Compound, International Journal of Pharmaceutics, Vol. 24, 1-17 (1985). In addition, wet milling techniques always result in the presence of a fraction of larger particles, which affects the time for the particles to completely dissolve.

Other efforts to reduce particle sizes include those such as described in U.S. Pat. Nos. 3,309,777 and 5,780,295. The '777 and '295 patents describes processes which include aerosolizing a biological suspension and impinging the aerosol particles onto a cold collecting surface, thereby encompassing each of the particles in a layer of pure water ice. The frozen aerosol particles are then removed from the cold surface and dried. The '777 and '295 patents teach the use of primarily water in the biological suspensions, which is not feasible when using poorly water soluble drug substances. Neither the '777 patent nor the '295 patent addresses the problems encountered when working with poorly water soluble drug substances.

Yet further efforts aimed at modifying particle structures are described in U.S. Pat. No. 3,932,943 and in WO 02/060411, which describe freezing materials by spraying those materials into a cryogenic liquid. However, the technologies described in these references have problems associated with recovering the particles from the cryogenic liquid, handling of the cryogenic liquid, and environmental issues.

U.S. Pat. Nos. 3,313,032 and 5,727,333 describe processes for drying materials from solution. However, neither of these patents address the need for improving the bioavailability and dissolution rates of poorly water soluble drug substances.

It would be an advantage to provide stable poorly water soluble pharmaceutical compositions in the micron or submicron particle size range which have improved bioavailability but do not have the problems associated with the above identified prior art.

SUMMARY OF THE INVENTION

In a first aspect, the present invention is a method for preparing micron-sized or submicron-sized drug particles comprising contacting a solution comprising a poorly water soluble drug substance and at least one freezable organic solvent with a cold surface so as to freeze the solution; and removing the organic solvent.

In a second aspect, the present invention is drug particles produced by a method which comprises: contacting a solution comprising a poorly water soluble drug substance and at least one freezable organic solvent with a cold surface so as to freeze the solution; and removing the organic solvent.

In a third aspect, the present invention is an apparatus for preparing drug particles comprising: a cold solid surface having a first side and an opposing second side; application means located proximate to the first side of the cold surface, the application means being adapted to permit a solution comprising a poorly water soluble drug substance and at least one freezable organic solvent to be applied to the first side of the cold surface so as to freeze the solution; cooling means located proximate to the second side of the cold surface, the cooling means adapted to cool the cold surface; removal means proximate to the cold surface for removing the frozen solution from the first side of the cold surface; solvent removal means for removing the organic solvent from the frozen solution; and means for transferring the frozen solution from the cold surface to the solvent removal means.

The present invention has the advantage of being able to process poorly water soluble drug substances, thereby improving the dissolution rates and bioavailability of those drug substances. Moreover, the present invention permits enhanced loading of the drug in the final drug formulation, as compared with those processes described in the above prior art. Moreover, certain aspects of the present invention permit easier processing of the resulting drug particles by avoiding solid-liquid separation steps and/or liquid-liquid separation steps or steps associated with handling cryogenic liquids.

BRIEF DESCRIPTION OF THE FIGURES

FIG. 1 is a plan view of one embodiment of an apparatus useful for the present invention.

FIG. 2 is a plan view of an alternative embodiment of an apparatus useful for the present invention.

FIG. 3 is a side view of an alternative embodiment of an apparatus useful for the present invention.

DETAILED DESCRIPTION OF THE INVENTION

FIG. 1 illustrates a first embodiment 10 of an apparatus that can be used to perform the present invention. A solution is first applied to a cold surface. The solution comprises a poorly water soluble drug substance and at least one freezable organic solvent. As used herein the term "poorly water soluble" means those drug substances having a solubility in water of less than about 10 mg/ml. The present invention has particular applicability to those drug substances having a solubility in water of less than about 1 mg/ml and even as low as 500 ng/ml.

Preferably, the drug substance is in essentially pure form and is dispersible in at least one liquid medium. Preferred drug substances include those intended for oral administration including, for example, analgesics, anti-inflammatory agents, anthelmintics, anti-arrhythmic agents, antibiotics (including penicillins), anticoagulants, antidepressants, antidiabetic agents, antiepileptics, antihistamines, antihypertensive agents, antimuscarinic agents, antimycobacterial agents, antineoplastic agents, immunosuppressants, antithyroid agents, antiviral agents, anxiolytic sedatives (hypnotics and neuroleptics), astringents, beta-adrenoceptor blocking agents, blood products and substitutes, cardiacinotropic agents, contrast media, corticosterioids, cough suppressants (expectorants and mucolytics), diagnostic agents, diagnostic imaging agents, diuretics, dopaminergics (antiparkinsonian agents), haemostatics, immunological agents, lipid regulating agents, muscle relaxants, parasympathomimetics, parathyroid calcitonin and biphosphonates, prostaglandins, radio-pharmaceuticals, sex hormones (including steroids), anti-allergic agents, stimulants and anoretics, sympathomimetics, thyroid agents, vasidilators and xanthines. A description of these classes of drugs and a listing of species within each class can be found in Martindale, The Extra Pharmacopoeia, Twenty-ninth Edition, The Pharmaceutical Press, London, 1989, the disclosure of which is hereby incorporate by reference.

The solution further comprises at least one freezable organic solvent. The organic solvent is required to solubilize the poorly water soluble drug. Preferably, the drug substance has a solubility range in the organic solvent of from about 0.1 to about 90 percent by weight. Particularly suitable organic solvents are selected from those that freeze at a relatively high temperature and have a boiling point that is relatively close to the freezing point. Preferably, the organic solvent has a freezing point of less than about 100° C. and more preferably less than about 75° C. Preferably, the organic solvent is selected from the group consisting of alcohols, ethers, halocarbons, hydrocarbons, halogenated hydrocarbons, aromatic hydrocarbons, esters, acetates, organic acids, amines, ketones, sulfones, nitriles, carbonates, aldehydes, and combinations thereof. Examples of specific suitable organic solvents include ethanol, isobutyl alcohol, methanol, n-butyl alcohol, isopropanol, n-amyl alcohol, n-heptyl alcohol, sec-octyl alcohol, cyclopentanol, n-octyl alcohol, benzyl alcohol, ethylene glycol, cycloheptanol, n-decyl alcohol, cyclooctanol, cyclohexanol, t-butanol, t-amyl alcohol, pentafluorophenol, methyl butynol, hexafluoroisopropanol, 2,2,2-trifluoroethanol, n-hexyl alcohol, 1,3,4-nitrocresol, methyl acetate, isobutyl acetate, n-propyl acetate, ethyl acetate, isoamyl acetate, n-butyl acetate, isopropyl acetate, n-amyl acetate, n-octyl acetate, sec-butyl acetate, toluene, ethylbenzene, m-xylene, o-xylene, p-xylene, mixed xylenes, benzene, cyclohexane, cycoheptane, 1,2,4,5-tetramethylbenzene, cyclopropane, gloxal, paraldhyde, trimethylacetaldehyde, dimethylformamide, beta-picoline, pyridine, morpholine, piperzine, 3,5-dichloropyridine, pyrazine, ethylenediamine, oxazole, diethylamine, triethylamine, methyl amine, dimethyl carbonate, di-t-butyl dicarbonate, methyl formate, isobutyl formate, isoamyl formate, n-propyl formate, ethyl formate, n-amyl formate, and dimethyl oxalate, diethylether, methyl-t-butyl ether, diisopropyl ether, 1,4-dioxane, tetrahydrofuran, 1,3,5-trioxane, p-dioxane, dimethyl ether, P-dichlorobenzene, pentafluorotoluene, hexafluorobenzene, 1,2,4,5-tetrafluorobenzene, 1,3,5-trifluorobenzene, chloroform, methylene chloride, carbon tetrachloride, 1,2-difluoro-1,1,2,2-tetrachloroethane, 1,1,1-trichloro-2,2,2-trifluoroethane, ethylene difluoride, 1,1,1-trichloroethane, 2,2-dichloropropane, 1,1,2-trichlroro-1,2,2-trifluoroethane, ethylene dichloride, perfluorocyclobutane, trans-dichloroethylene, 1-bromo-1-chloro-2,2,2-trifluoroethane, and pefluorodecane, trans-1,2-12,-dichlorethene, n-hexane, n-heptane, n-octane, n-decane, 2,2,3,3-tetramethylbutane, bicyclo(2.2.1)hept-2-ene, 2,3,4-trimethyl-1-pentene, 2,5-dimethyl-2,4-hexadiene, tetranitromethane, cis-1,3,5-hexatriene, neopentane, 2,2,3-trimethylbutane, dimethylacetylene, diacetylene, acetone, methyl ethyl ketone, methyl iso-butyl ketone, methyl butyl ketone, cylclopentanone, methyl-t-butyl ketone, diisobutyl ketone, diethyl ketone, dipropyl ketone, cyclohexanone, methyl heptyl ketone, acetonitrile, fumaronitrile, formic acid, glacial acetic acid, glycolic acid, propionic acid, trifluoroacetic acid, dimethyl sulfoxide and combinations thereof. When combinations of solvents are used, the ratios of the solvents used is not critical and will depend upon the desired freezing point of the solution as well as the desired level of dissolution of the particular drug that will be dissolved in the combination of solvents.

Even more preferably, the freezable organic solvent is selected from methylene chloride, cyclopentanol, t-amyl alcohol, p-xylene, t-butanol, acetonitrile, tetrahydrofuran, cyclohexane, trifluoroethanol, glycolic acid, acetic acid, cyclohexanone, methyl t-butyl ketone, diethyl ketone, and combinations thereof. Most preferably, the freezable organic solvent is selected from those generally regarded as being pharmaceutically acceptable.

Optionally, the solution further comprises at least one stabilizer. Alternatively, the optional stabilizer(s) are added after the solution is frozen. The stabilizer inhibits crystal growth, aggregation and agglomeration of the drug particles. The choice of stabilizer or stabilizers will depend upon the drug molecule. Generally, polymeric stabilizers are preferred. Examples of particle stabilizers include phospholipids, surfactants, polymeric surfactants, vesicles, polymers, including copolymers and homopolymers and biopolymers, and/or dispersion aids. Suitable surfactants include gelatin, casein, lecithin, phosphatides, gum acacia, cholesterol, tragacanth, fatty acids and fatty acid salts, benzalkonium chloride, glycerol mono and di fatty acid esters and ethers, cetostearyl alcohol, cetomacrogol 1000, polyoxyethylene castor oil derivatives, polyoxyethylene sorbitan fatty acid esters, e.g., the commercially available Tweens, polyethylene glycols, poly(ethylene oxide/propylene oxide) copolymers, e.g., the commercially available Poloxomers or Pluronics, polyoxyethylene fatty acid ethers, e.g., the commercially available Brijs, polyoxyethylene fatty acid esters, sorbitan fatty acid esters, e.g., the commercially available Spans, colloidal silicon dioxide, phosphates, sodium dodecylsulfate, carboxymethylcellulose calcium, carboxymethylcellulose sodium, methylcellulose, hydroxyethylcellulose, hydroxypropylcellulose, hydroxypropylmethylcellulose, noncrystalline cellulose, magnesium aluminum silicate, triethanolamine, polyvinyl alcohol (PVA), sodium lauryl sulfate, polyvinylpyrrolidone (PVP), poly(acrylic acid), and other anionic, cationic, zwitterionc and nonionic surfactants. Other suitable stabilizers are described in detail in the Handbook of Pharmaceutical Excipients, published jointly by the American Pharmaceutical Association and The Pharmaceutical Society of Great Britain, the Pharmaceutical Press, 1986, which is incorporated by reference herein. Such stabilizers are commercially available and/or can be prepared by techniques known in the art.

Generally, the amount of stabilizer added to the solution will depend upon the dosage form of the drug and the type of drug. Preferably, the stabilizer is added to the solution in a concentration of less than 90%, more preferably less than 70% and even more preferably less than 50%.

If a stabilizer is used, water can optionally added to the solution in order to assist in solubilizing the stabilizer, even though water would not be useful to solubilize the poorly water soluble drug.

In one embodiment, the stabilizer is characterized as a surfactant. Surfactants that can be advantageously employed herein can be readily determined by those skilled in the art and include various nonionic, anionic, cationic, and amphoteric surfactants, or a blend of those surfactants. Preferred surfactants are those which significantly reduce the tendency for the oil droplets of the discontinuous phase to agglomerate. Examples of nonionic surfactants include the polyalkylene glycol ethers and condensation products of aliphatic alcohols, aliphatic amines, or fatty acids with ethylene oxide or propylene oxide; polyvinyl alcohols of different molecular weights and degree of hydrolyzation; polyvinyl pyrrolidones; and the surfactants of the Brij, Tween, and Span series. Anionic surfactants include salts of alkyl aryl sulphonic acids, sulphated polyglycol ethers, and ethers of sulphosuccinic acid. Cationic surfactants include quaternary ammonium compounds and fatty amines.

The cold solid surface comprises a first side and an opposing second side. The solution is applied to the cold solid surface by way of application means located proximate to the first side of the cold solid surface. In the embodiment shown in FIG. 1, sprayer 11 is the means for applying the solution to the cold surface. Sprayer 11 can be a standard, commercially available sprayer or can be a specially-designed sprayer. Any means for applying the solution to the cold surface can be used, such as means utilizing gravity, utilizing a difference in pressure, utilizing an electric charge and/or utilizing a temperature differential. Alternatively, a dropper 21 such as that shown in FIG. 2 may be used to apply the solution to the cold surface in dropwise fashion, or a roller, a brush or other capillary action applicator may be used. Alternatively, vacuum may be used to pull the solution onto the cold surface. Other types of application means known to those skilled in the art may be used as well.

Figure 2:
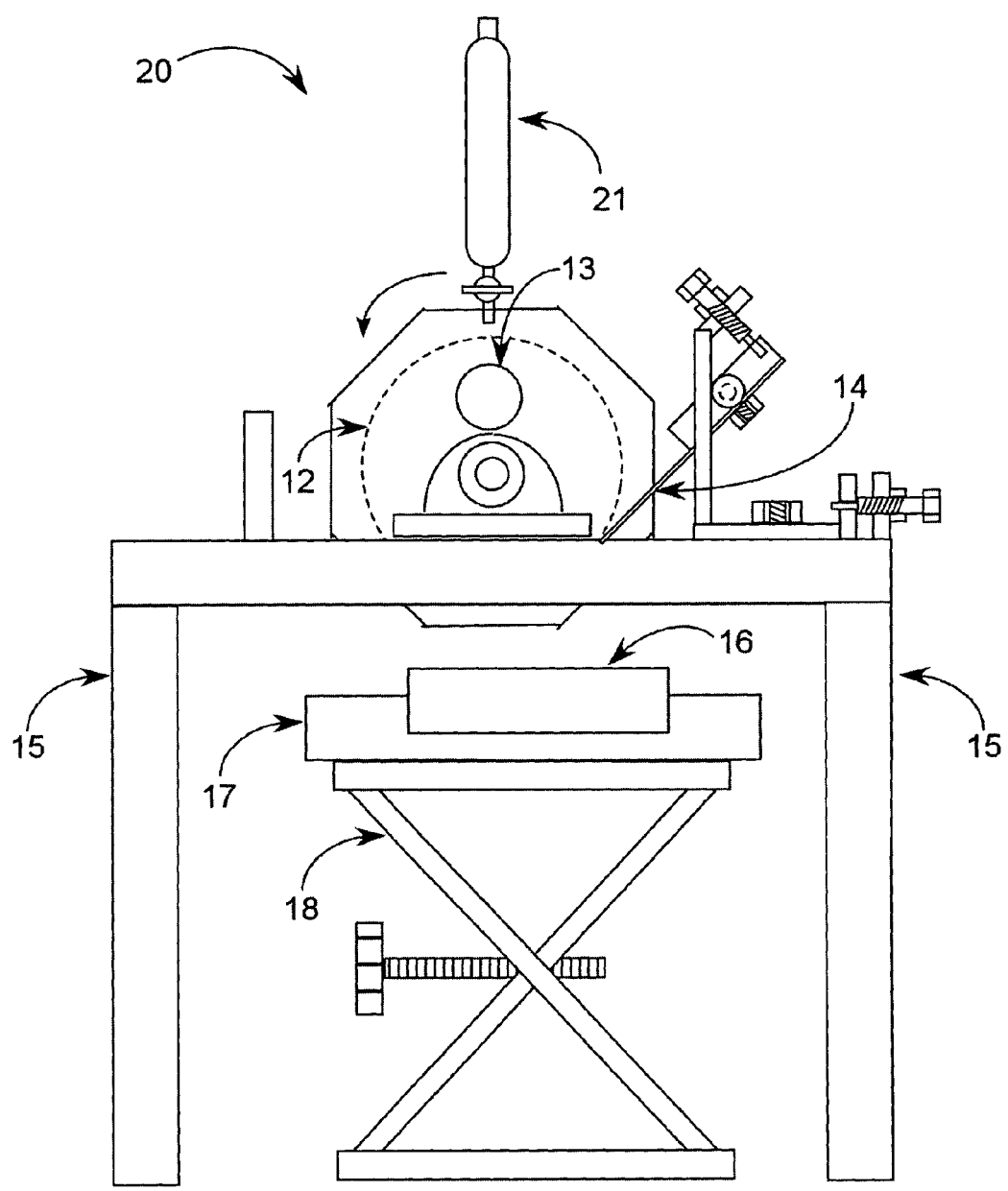

In the embodiment shown in FIGS. 1 and 2, the cold solid surface comprises a cylinder 12 that is capable of being maintained at low temperatures and can be rotated. However, any solid surface may be used, and it is not necessary that the surface be curved or that it move. A flat solid surface may also be used, or a curved surface that does not rotate may be used as well, so long as the surface is in a sold state and can be maintained at very low temperatures so as to substantially freeze the solution upon contact. Examples of solid surfaces include but are not limited to a rotating drum, a belt, a tray and the like.

The rate at which the solution is applied to the cold surface should be sufficient such that the solution is substantially frozen soon after contact with the cold surface. Preferably, the solution is substantially frozen in less than one minute upon contact with the cold surface. More preferably, the solution is applied to the cold surface such that the solution substantially freezes in less than one second upon contact with the cold surface. The solution should be applied to the surface such that the thickness of the resulting film layer of solution formed on the cold surface is sufficient to freeze within seconds upon contact. Preferably, the rate of application results in a film thickness of less than 5 millimeters, more preferably, less than about 1 mm, even more preferably less than about 0.2 mm, and yet even more preferably less than about 0.05 mm. If the film of solution is not substantially frozen within seconds of contact with the cold surface, the solution is being applied too quickly.

The material of construction for the cold surface can be any material that is capable of being cooled to the desired temperature. Preferably, the material of construction is one that enables good heat transfer. Examples of particularly suitable materials of construction for the cold surface include metals, metal alloys, glass, and ceramics.

The temperature at which the solution is held prior to being applied to the cold surface is not critical.

Figure 3:
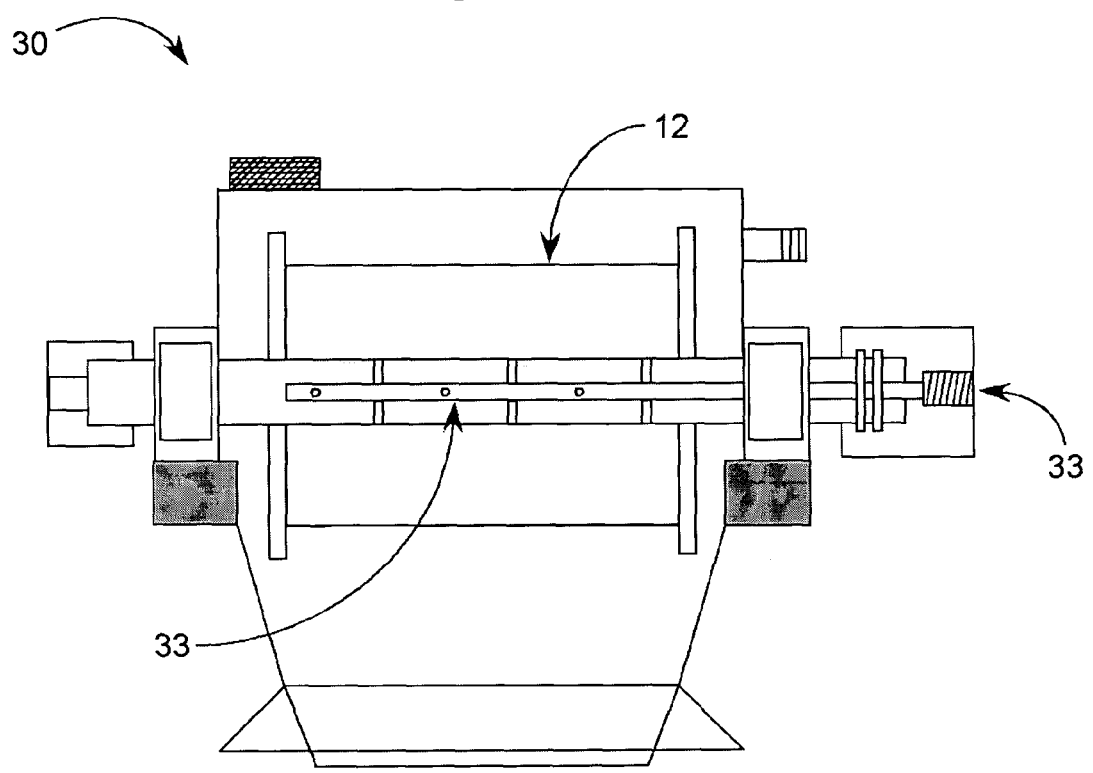

The present invention includes cooling means located proximate to the second side of the cold solid surface, the cooling means adapted to cool the surface. The cooled solid surface can be cooled using any suitable means, including those utilizing a cryogenic solid, a cryogenic gas, a cryogenic liquid, or a heat transfer fluid capable of reaching cryogenic temperatures. A cryogenic solid is defined as a material that sublimes below the freezing point of water, such as, for example, carbon dioxide. A cryogenic gas means a material that is a gas below the freezing point of water, such as, for example, nitrogen. A cryogenic liquid is a material that is liquid below the freezing point of water, such as, for example, liquid nitrogen. In the embodiments shown in FIGS. 1 and 2, a hole 13 in cylinder 12 permits insertion of dry ice into the inside of cylinder 12 so as to cool the surface of cylinder 12. In the embodiment shown in FIG. 3, a cryogenic heat transfer agent 33 such as nitrogen or liquid carbon dioxide may be placed in contact with the cold surface, either directly or indirectly, so as to cool the surface. Other means for cooling the surface known to those skilled in the art may be used as well.

The temperature at which the cold surface should be cooled to will depend upon the organic solvent or solvents used in the solution. The cold solid surface should be cooled to a temperature that is below the freezing point of the freezable organic solvent prior to contacting the solution with the cold solid surface so as to ensure that the solution substantially freezes upon contact with the solid surface. The difference between the freezing point of the freezable organic solvent and the temperature of the cold surface will impact the rate of freezing of the solution.

As used herein, the term "frozen solution" is defined to mean poorly water soluble drug particles and, optionally, one or more excipients, suspended in a frozen organic solvent matrix. Such frozen solution is formed once the solution is substantially frozen within seconds after contact with the cold surface.

Preferably, the cold surface is cooled to a temperature of at least 5° C. below the freezing point of the organic solvent, more preferably at least 30° C. below the freezing point of the organic solvent, even more preferably at least 50° C. below the freezing point of the organic solvent, and most preferably at least 75° C. below the freezing point of the organic solvent. Desirably, the cold surface is maintained at a low temperature for entire period of time during which the process of the present invention is being carried out.

The present invention also includes means for removing the frozen solution from the cold surface. As shown in FIGS. 1 and 2, one example of means for transferring the frozen solution includes a knife blade assembly 14 which flakes the frozen solution off of the cold surface and then allows the frozen solution to be gravity fed to a collecting surface or directly to further processing. Vibration, pressure, a brush or a blower or other methods utilizing a pressure differential are other appropriate means for removing the frozen solution from the cold surface. Alternatively, a non-stick coating on the cold surface would permit automatic removal of the frozen solution.

FIGS. 1 and 2 also show a product tray 16 used as a collecting surface for the frozen solution once removed from the cylinder 12, and a secondary tray 17 as optional means for cooling product tray 16. By cooling the product tray, the solution is kept frozen until ready for further processing.

Means for transferring the frozen solution to subsequent processing step might be necessary for the present invention as well. In embodiments such those as shown in FIGS. 1-2, the frozen solution is gravity fed to the subsequent processing steps. In other embodiments, a conveyor could be used to transfer the frozen solution.

Solvent removal means are used to remove the organic solvent from the frozen solution, thereby generating the resulting drug particles. Suitable solvent removal means include sublimation and evaporation. Examples of sublimation techniques include but are not limited to lyophilization and atmospheric freeze drying, as known by those skilled in the art of solvent removal. Examples of evaporation techniques include but are not limited to distillation techniques and spray drying techniques, as known by those skilled in the art of solvent removal. In order to employ such evaporation techniques, the frozen solution is desirably first dispersed in a liquid that is miscible with the organic solvent but that does not solubilize the drug substance, such as, for example, water.

The mean volume average particle size of the resulting drug particles after the particles are dispersed in water is from 0.05 microns to 150 microns, as measured using light scattering techniques. More preferably, the mean volume average particle size is 50 microns or less, even more preferably 25 microns or less, yet even more preferably 5 microns or less, and most preferably 1 micron or less.

The resulting drug particles have a high surface area relative to particles that are not processed using the present invention. Advantageously, a high surface area can contribute to a relatively fast dissolution time. Preferably, the particles prepared according to the present invention have a surface area at least 2 $m^2/g$, more preferably at least 5 $m^2/g$, and even more preferably at least 10 $m^2/g$, as measured using BET techniques known to those skilled in the art.

The drug particles may be combined with any pharmaceutically-acceptable carrier in order to form a pharmaceutical formulation capable of, preferably, oral administration. The compositions of the inventions may also include optional excipients such as standard fillers, binders, or disintegrants readily known by those skilled in the art.

The resulting drug particles exhibit enhanced in vitro dissolution rates as compared to the drug before being processed using the present invention. Preferably, the drug particles processed using the present invention exhibit an in vitro dissolution rate of at least 1.5 times better than that of the unprocessed drug, more preferably at least 5 times better than that of the unprocessed drug, and even more preferably at least 10 times better than that of the unprocessed drug, as measured using standard in vitro dissolution methods known to those skilled in the art. For example, within 2 minutes, if the unprocessed drug is 20% dissolved, then particles processed using the present invention would be at least 30% dissolved.

Surprisingly, the resulting drug particles are substantially crystalline in nature, despite the fact that the present invention involves rapid freezing.

The invention will be further clarified by a consideration of the following examples, which are intended to be purely exemplary of the present invention. All parts and percentages are by weight, unless otherwise specified.

EXAMPLES

Materials

Cyclosporin A is a drug substance that was purchased from POLI Industria Chimica S.P.A.

Danazol is a drug substance that was purchased from Spectrum Chemical Co., & Diosynth Co.

Ketoconazole, ketoprofen, naproxen, nifedipine, prednisone, triamcinalone acetonide, carbamazepine, and hydrocortisone acetate are drug substances that were purchased from the Spectrum Chemical Co.

Pluronic F-127, is a stabilizer that was purchased from the Sigma Chemical Co.

Pluronic F-108, Pluronic F-88 are stabilizers that were purchased from the BASF Co.

Pluronic F-68, polyvinylpyrrolidone (PVP, 10K, 29K, 55K), SPAN 40, SPAN 60, and polyethylene glycol (PEG, 10K), are stabilizers that were purchased from the Aldrich Chemical Co.

p-Xylene, t-amyl alcohol, 1,3,5-trioxane, sec-butyl acetate and cyclopentanol are solvents that were purchased from the Aldrich Chemical Co.

t-Butanol, acetonitrile, acetone, tetrahydrofuran and ethyl acetate are solvents that were purchased from Fisher Scientific Co.

Analytical Methods

Particle Size Analysis. Analysis was performed on the bulk drug powder as received and on the powders prepared in Examples 1-60, after being redispersed in water, using a Beckman Coulter Counter.

USP Dissolution Apparatus Method 2. Dissolution obtained using the following method is also referred to herein as "in vitro dissolution". The dissolution media used varied with the drug substance, and is specified below. The dissolution media was heated to 37° C. and degassed. Dissolution was performed utilizing three vessels per experiment. 11 to 12 mg of drug particles prepared according to the present invention was added to each vessel for dissolution analysis. Dissolution samples were filtered automatically into test tubes containing 0.1 mL of acetonitrile, mixed with a vortex mixer, filtered and analyzed by HPLC. Samples were taken at 2, 5, 10, 15, 20, 30, 60, and 120 minutes. At the 60 min. point the agitation speed was increased to 200 rpm to ensures complete dissolution by 120 minutes. The 120 min. reading is the infinity time reading and the infinity time is used to calculate the potency. Dissolution times were measured for the bulk drug substance as received as well as the drug particles prepared according to the present invention for each of Examples 1-60. Dissolution Media for the various drug substances used in Examples 1-60 were as follows:

For Naproxen, Carbamazapine & Ketoprofen: The dissolution media was deionized water containing 5.0 wt. % sodium chloride.

For Danazol: The dissolution media was deionized water containing 0.75 wt. % SLS, and 1.21 wt. % Tris(hydroxymethyl)aminomethane, and was adjusted to pH 9.

For Cyclosporin A: The dissolution media was deionized water containing 0.1 wt. % SLS.

For Ketoconazole: The dissolution media was deionized water containing 0.5 wt. % SLS.
For Nifedipine: The dissolution media was deionized water containing 0.3 wt. % SLS and 3.0 wt. % sodium chloride.
For Prednisone & Triamcinalone Acetonide: The dissolution media was deionized water containing 10.0 wt. % sodium chloride.
For Hydrocortisone Acetate: The dissolution media was deionized water containing 0.3 wt. % sodium sodium dodecylsulfate (SDS).
Percent Crystallinity. Crystallinity was determined by X-ray diffraction methods using a Bruker D-8 automated diffractometer.
Atmospheric Freeze Drying (ATMFD). ATMFD was one method of solvent removal used in the following examples. Heat transfer fluid was circulated through the circulating jacket of the heat exchanger, that was used to cool the drying gas then to the jacket of the ATMFD unit. Chilled nitrogen gas is flowed through the bottom of the ATMFD unit to sublime the solvent(s) away from the drug (s) and fluidizing the solids. The ATMFD unit and the nitrogen gas temperature are slowly warmed to ambient temperature. After the ATMFD portion of the process was complete the solid was collected from either the cyclone or the ATMFD Unit.
Freeze Drying. Freeze drying was an alternative solvent removal method used in some of the following examples. The frozen solution that was prepared was transferred to ajar cooled with dry ice. The processed solid in the chilled container was placed on a Virtis freeze dryer and dried for app. 12-24 hr at approximately 100 mtorr vacuum. For each of Examples 1-60, solutions were made using the materials listed in Table A.

TABLE A

| Example | Drug | Wt % drug | Solvent(s) | Wt % solvent | Stabilizer(s) | Wt % stabilizer |
|---|---|---|---|---|---|---|
| 1 | Danazol (bottle) | 1.44 | t-Butanol | 95.68 | Pluronic F-127, & PVP(10k) (50/50) wt. % ratio | 2.88 |
| 2 | Ketoconazole (sprayed) | 1.22 | t-Butanol | 97.56 | Pluronic F-127 | 1.22 |
| 3 | Danazol (sprayed) | 2.13 | t-Butanol | 95.74 | Pluronic F-127 | 2.13 |
| 4 | Carbamazepine | 1.92 | t-Butanol | 96.16 | Pluronic F-127 | 1.92 |
| 5 | Carbamazepine | 0.50 | p-Xylene | 99.00 | Pluronic F-127 | 0.50 |
| 6 | Carbamazepine | 1.92 | t-Butanol | 96.16 | Pluronic F-127 | 1.92 |
| 7 | Carbamazepine | 0.95 | t-Butanol | 98.10 | Pluronic F-88 | 0.95 |
| 8 | Carbamazepine | 0.95 | t-Butanol | 98.08 | PVP(10k) | 0.97 |
| 9 | Carbamazepine | 1.00 | t-Butanol | 98.00 | Pluronic F-127, & PVP(10k) (50/50) wt. % ratio | 1.00 |
| 10 | Cyclosporin A | 1.92 | t-Butanol | 96.16 | Pluronic F-127 | 1.92 |
| 11 | Cyclosporin A | 1.92 | t-Butanol | 96.16 | Pluronic F-127 | 1.92 |
| 12 | Danazol | 2.83 | t-Butanol | 94.34 | Pluronic F-127 | 2.83 |
| 13 | Danazol | 3.70 | t-Butanol | 92.60 | Pluronic F-127 | 3.70 |
| 14 | Danazol | 4.55 | t-Butanol | 90.90 | Pluronic F-127 | 4.55 |
| 15 | Danazol | 1.61 | t-Butanol | 96.78 | Pluronic F-127 | 1.61 |
| 16 | Danazol | 1.47 | t-Butanol | 98.04 | Pluronic F-108, & PVP(55k) (50/50) wt. % ratio | 0.49 |
| 17 | Danazol | 0.93 | t-Butanol | 98.08 | PVP(10k) | 0.99 |
| 18 | Danazol | 0.90 | t-Butanol | 98.14 | PVP(29k) | 0.96 |
| 19 | Danazol | 0.98 | t-Butanol | 98.04 | PVP(55k) | 0.98 |
| 20 | Danazol | 1.04 | t-Butanol | 97.93 | PEG(10k) | 1.03 |
| 21 | Hydrocortisone Acetate | 1.00 | t-Butanol | 98.00 | Pluronic F-127 | 1.00 |
| 22 | Hydrocortisone Acetate | 0.97 | t-Butanol | 98.03 | Pluronic F-127, & PEG(10k) (50/50) wt. % ratio | 1.00 |
| 23 | Hydrocortisone Acetate | 0.92 | t-Butanol | 98.17 | Pluronic F-68 | 0.91 |
| 24 | Hydrocortisone Acetate | 0.95 | t-Butanol | 98.11 | PEG(10k) | 0.94 |
| 25 | Ketoconazole | 1.17 | t-Butanol | 97.66 | Pluronic F-127 | 1.17 |
| 26 | Ketoconazole | 0.98 | t-Butanol | 98.04 | Pluronic F-127 | 0.98 |
| 27 | Ketoprofen | 1.92 | t-Butanol | 96.16 | Pluronic F-127 | 1.92 |
| 28 | Ketoprofen | 1.92 | t-Butanol | 96.16 | Pluronic F-127 | 1.92 |
| 29 | Ketoprofen | 1.00 | t-Butanol | 97.93 | Pluronic F-88 | 1.07 |
| 30 | Naproxen | 1.61 | t-Butanol | 96.78 | Pluronic F-127 | 1.61 |
| 31 | Naproxen | 1.61 | t-Butanol | 96.78 | Pluronic F-127 | 1.61 |
| 32 | Naproxen | 1.00 | t-Butanol, & t-Amyl Alcohol (60/40) wt. % ratio | 98.00 | Pluronic F-127 | 1.00 |
| 33 | Naproxen | 1.60 | t-Butanol | 98.00 | Pluronic F-127, & PVP(29k) (50/50) wt. % ratio | 0.40 |
| 34 | Naproxen | 1.40 | p-Xylene, & 1,3,5-Trioxane | 98.00 | Pluronic F-127 | 0.60 |

TABLE A-continued

| Example | Drug | Wt % drug | Solvent(s) | Wt % solvent | Stabilizer(s) | Wt % stabilizer |
|---|---|---|---|---|---|---|
| | | | (80/20) wt. % ratio | | | |
| 35 | Naproxen | 9.94 | t-Butanol | 80.10 | Pluronic F-127 | 9.96 |
| 36 | Naproxen | 1.00 | t-Butanol, & Cyclopentanol (80/20) wt. % ratio | 97.99 | Pluronic F-127 | 1.01 |
| 37 | Naproxen | 1.67 | t-Butanol, (deionized water also added to assist in solubilizing the stabilizer). (50/50) wt. % ratio | 96.67 | Pluronic F-127 | 1.66 |
| 38 | Naproxen | 1.00 | t-Butanol, & Acetonitrile (90/10) wt. % ratio | 98.00 | Pluronic F-127 | 1.00 |
| 39 | Naproxen | 13.73 | t-Butanol, & Acetone (90/10) wt. % ratio | 80.38 | Pluronic F-127 | 5.89 |
| 40 | Naproxen | 1.00 | t-Butanol, & Ethyl Acetate (90/10) wt. % ratio | 98.00 | Pluronic F-127 | 1.00 |
| 41 | Naproxen | 1.00 | t-Butanol, & sec-Butyl Acetate (90/10) wt. % ratio | 98.00 | Pluronic F-127 | 1.00 |
| 42 | Naproxen | 1.00 | t-Butanol, & 1,3,5-Trioxane (50/50) wt. % ratio | 98.00 | Pluronic F-127 | 1.00 |
| 43 | Naproxen | 4.11 | p-Xylene | 94.13 | Pluronic F-127 | 1.76 |
| 44 | Naproxen | 0.95 | t-Butanol | 98.11 | SPAN 40 | 0.94 |
| 45 | Naproxen | 0.94 | t-Butanol | 98.10 | Pluronic F-127 & SPAN 40 (50/50) wt. % ratio | 0.96 |
| 46 | Naproxen | 1.00 | t-Butanol | 98.01 | SPAN 60 | 0.99 |
| 47 | Naproxen | 0.98 | t-Butanol | 98.01 | Pluronic F-127 & SPAN 60 (50/50) wt. % ratio | 1.01 |
| 48 | Nifedipine | 1.92 | t-Butanol | 96.16 | Pluronic F-127 | 1.92 |
| 49 | Nifedipine | 1.92 | t-Butanol | 96.16 | Pluronic F-127 | 1.92 |
| 50 | Nifedipine | 0.95 | t-Butanol | 98.06 | Pluronic F-127, & PVP(55k) (50/50) wt. % ratio | 0.99 |
| 51 | Prednisone | 0.89 | t-Butanol | 98.22 | Pluronic F-127 | 0.89 |
| 52 | Prednisone | 0.89 | t-Butanol | 98.22 | Pluronic F-127 | 0.89 |
| 53 | Prednisone | 0.94 | t-Butanol | 98.07 | Pluronic F-108 | 0.99 |
| 54 | Triamcinalone Acetonide | 1.92 | t-Butanol | 96.16 | Pluronic F-127 | 1.92 |
| 55 | Triamcinalone Acetonide | 1.92 | t-Butanol | 96.16 | Pluronic F-127 | 1.92 |
| 56 | Triamcinalone Acetonide | 0.76 | t-Butanol | 98.47 | PVP(10k) | 0.77 |
| 57 | Naproxen | 2.50 | t-Butanol | 94.99 | Pluronic F-127 | 2.51 |
| 58 | Naproxen | 5.83 | t-Butanol | 91.67 | Pluronic F-127 | 2.50 |
| 59 | Naproxen | 5.93 | Acetonitrile | 91.41 | Pluronic F-127 | 2.66 |
| 60 | Naproxen | 3.67 | Tertahydrofuran, (deionized water also added to assist in solubilizing the stabilizer). (68/32) wt. % ratio | 94.73 | Pluronic F-127 | 1.60 |

Example 1

A 125-mL freeze-drying bottle was cooled to −78° C. in a dry-ice acetone bath. The prepared solution was slowly pipetted into the cooled freeze-drying bottle. The frozen solid in the freeze drying bottle was then placed on a freeze drying unit and allowed to lyophylize until completely dry, resulting in 0.9 g of flowable white powder. Particle size analysis results and dissolution times determined both before and after processing are shown in Table B.

Examples 2 and 3

The apparatus shown in FIG. 1 was used. Cylinder 12 was cooled to −78° C. with dry ice. The solution was sprayed onto cylinder 12 for approximately 10 minutes. The resulting frozen solid was removed by use of knife blade assembly 14, and was collected in cooled product collection tray 16. The collected material was transferred by hand to a solvent removal unit. Particle size analysis results and dissolution times determined both before and after carrying out the process of the present invention are shown in Table B.

Examples 4 through 56

The apparatus shown in FIG. 2 was used. Cylinder 12 was cooled to −78° C. with dry ice. The solution was dripped onto cylinder 12 for approximately 10 minutes using an addition funnel. The resulting frozen solid was removed by use of knife blade assembly 14 and collected in a cooled product collection tray 16. The collected product was then transferred by hand to the solvent removal step. Particle size analysis results and dissolution times determined both before and after carrying out the process of the present invention are shown in Table B.

Examples 57 through 60

The apparatus shown in FIG. 2 was used. Cylinder 12 was cooled to −78° C. with dry ice. The solution was dripped onto cylinder 12 for approximately 10 minutes using an addition funnel. The resulting frozen solid was removed by use of knife blade assembly 14 and collected in a cooled product collection tray 16. The collected product was dispersed in deionized water. The dispersed solid/aqueous/solvent slurry was then taken directly into the solvent removal step. Particle size analysis results and dissolution times determined both before and after carrying out the process of the present invention are shown in Table B.

TABLE B

| Example | Drug | Drying Method | PSA* of bulk drug (microns) | PSA* of processed drug (microns) | Dissolution of bulk drug after 2 minutes (wt %) | Dissolution of processed drug after 2 minutes (wt %) | % crystallinity |
|---|---|---|---|---|---|---|---|
| 1 | Danazol (bottle) | Freeze dried | 24.86 | 0.301 | 56.42 | 97.1 | — |
| 2 | Ketoconazole (sprayed) | ATMFD | 13.5 | 7.334 | 26.1 | 100.77 | — |
| 3 | Danazol (sprayed) | ATMFD | 24.86 | 23.47 | 56.42 | 103.03 | — |
| 4 | Carbamazepine | ATMFD | 391.4 | 30.07 | 4.83 | 74.62 | 79.2 |
| 5 | Carbamazepine | ATMFD | 391.4 | 22.58 | 4.83 | 77.30 | — |
| 6 | Carbamazepine | Freeze dried | 391.4 | 54.13 | 4.83 | 48.23 | — |
| 7 | Carbamazepine | Freeze dried | 391.4 | 103.10 | 4.83 | 77.52 | — |
| 8 | Carbamazepine | Freeze dried | 391.4 | 92.43 | 4.83 | 65.37 | — |
| 9 | Carbamazepine | Freeze dried | 391.4 | 74.26 | 4.83 | 77.50 | — |
| 10 | Cyclosporin A | ATMFD | 53.89 | 38.02 | 3.39 | 86.4 | amorphous |
| 11 | Cyclosporin A | Freeze dried | 53.89 | 22.04 | 3.39 | 26.02 | — |
| 12 | Danazol | ATMFD | 24.86 | 17.60 | 56.42 | 100.17 | 70.4 |
| 13 | Danazol | ATMFD | 24.86 | 43.29 | 56.42 | 99.22 | — |
| 14 | Danazol | ATMFD | 24.86 | 34.54 | 56.42 | 104.15 | — |
| 15 | Danazol | Freeze dried | 24.86 | 15.47 | 56.42 | 99.75 | — |
| 16 | Danazol | Freeze dried | 24.86 | 7.011 | 56.42 | 97.55 | — |
| 17 | Danazol | Freeze dried | 24.86 | 4.377 | 56.42 | 101.41 | — |
| 18 | Danazol | Freeze dried | 24.86 | 108.50 | 56.42 | 103.01 | — |
| 19 | Danazol | Freeze dried | 24.86 | 20.80 | 56.42 | 89.52 | — |
| 20 | Danazol | Freeze dried | 24.86 | 16.53 | 56.42 | 93.31 | — |
| 21 | Hydrocortisone Acetate | ATMFD | 17.07 | 7.447 | 21.16 | 97.46 | 91.2 |
| 22 | Hydrocortisone Acetate | Freeze dried | 17.07 | 3.949 | 21.16 | 100.49 | — |
| 23 | Hydrocortisone Acetate | Freeze dried | 17.07 | 9.740 | 21.16 | 94.65 | — |
| 24 | Hydrocortisone Acetate | Freeze dried | 17.07 | 27.94 | 21.16 | 91.10 | — |
| 25 | Ketoconazole | ATMFD | 13.50 | 11.64 | 26.10 | 98.85 | 94.6 |
| 26 | Ketoconazole | Freeze dried | 13.50 | 76.66 | 26.10 | 78.8 | — |
| 27 | Ketoprofen | ATMFD | 42.73 | 27.60 | 2.81 | 92.39 | 74.7 |
| 28 | Ketoprofen | Freeze dried | 42.73 | 82.93 | 2.81 | 57.06 | — |
| 29 | Ketoprofen | Freeze dried | 42.73 | 91.82 | 2.81 | 72.70 | — |
| 30 | Naproxen | ATMFD | 24.07 | 13.28 | 0.29 | 64.05 | — |
| 31 | Naproxen | Freeze dried | 24.07 | 2.193 | 0.29 | 71.57 | 90.5 |
| 32 | Naproxen | Freeze dried | 24.07 | 0.847 | 0.29 | 99.96 | — |
| 33 | Naproxen | Freeze dried | 24.07 | 0.859 | 0.29 | 70.23 | — |
| 34 | Naproxen | Freeze dried | 24.07 | 9.858 | 0.29 | 76.77 | — |
| 35 | Naproxen | Freeze dried | 24.07 | 1.272 | 0.29 | 65.77 | — |
| 36 | Naproxen | Freeze dried | 24.07 | 56.33 | 0.29 | 94.77 | — |
| 37 | Naproxen | Freeze dried | 24.07 | 84.76 | 0.29 | 70.69 | — |
| 38 | Naproxen | Freeze dried | 24.07 | 10.76 | 0.29 | 70.54 | — |
| 39 | Naproxen | Freeze dried | 24.07 | 18.24 | 0.29 | 76.43 | — |
| 40 | Naproxen | Freeze dried | 24.07 | 44.04 | 0.29 | 88.77 | — |
| 41 | Naproxen | Freeze dried | 24.07 | 33.80 | 0.29 | 87.16 | — |

TABLE B-continued

| Example | Drug | Drying Method | PSA* of bulk drug (microns) | PSA* of processed drug (microns) | Dissolution of bulk drug after 2 minutes (wt %) | Dissolution of processed drug after 2 minutes (wt %) | % crystallinity |
|---|---|---|---|---|---|---|---|
| 42 | Naproxen | Freeze dried | 24.07 | 0.807 | 0.29 | 74.17 | — |
| 43 | Naproxen | Freeze dried | 24.07 | 1.114 | 0.29 | 78.46 | — |
| 44 | Naproxen | Freeze dried | 24.07 | 118.40 | 0.29 | 37.34 | — |
| 45 | Naproxen | Freeze dried | 24.07 | 79.69 | 0.29 | 44.31 | — |
| 46 | Naproxen | Freeze dried | 24.07 | 74.51 | 0.29 | 34.71 | — |
| 47 | Naproxen | Freeze dried | 24.07 | 67.90 | 0.29 | 40.82 | — |
| 48 | Nifedipine | ATMFD | 244.9 | 39.53 | 4.70 | 83.34 | 77.9 |
| 49 | Nifedipine | Freeze dried | 244.9 | 16.45 | 4.70 | 56.65 | — |
| 50 | Nifedipine | Freeze dried | 244.9 | 19.13 | 4.70 | 76.75 | — |
| 51 | Prednisone | ATMFD | 3.263 | 15.30 | 0.97 | 81.42 | 81.7 |
| 52 | Prednisone | Freeze dried | 3.263 | 11.52 | 0.97 | 89.19 | — |
| 53 | Prednisone | Freeze dried | 3.263 | 14.31 | 0.97 | 80.24 | — |
| 54 | Triamcinalone Acetonide | ATMFD | 7.707 | 11.60 | 5.38 | 47.56 | 38.2 |
| 55 | Triamcinalone Acetonide | Freeze dried | 7.707 | 9.176 | 5.38 | 51.90 | — |
| 56 | Triamcinalone Acetonide | Freeze dried | 7.707 | 15.08 | 5.38 | 32.31 | — |
| 57 | Naproxen | Freeze dried | 24.07 | 3.622 | 0.29 | 63.20 | — |
| 58 | Naproxen | Freeze dried | 24.07 | 3.282 | 0.29 | 59.84 | — |
| 59 | Naproxen | Freeze dried | 24.07 | 6.477 | 0.29 | 70.23 | — |
| 60 | Naproxen | Freeze dried | 24.07 | 10.59 | 0.29 | 82.22 | — |

*PSA means "particle size analysis".

What is claimed is:

1. A method for enhancing the dissolution rate of drug particles comprising:
   (a) cooling a cold solid surface to less than 5° C.;
   (b) selecting a freezable organic solvent with a freezing point close to the temperature of the cold surface and into which a poorly water soluble drug substance dissolves;
   (c) dissolving the poorly water soluble drug substance in the freezable organic solvent into a solution;
   (d) contacting the solution with the cold solid surface so as to freeze the solution, wherein the rate of freezing of the solution is determined by the difference between the freezing point of the freezable organic solvent and the temperature to which the cold solid surface is cooled in step (a); and
   (e) removing the organic solvent, wherein the resulting particles have a mean volume average particle size from less than 0.05 microns to 24 microns, a surface area of at least 2 m²/g and exhibit an in vitro dissolution rate of at least 1.5 times better than that of the unprocessed drug.

2. The method according to claim 1 wherein the cold surface is cooled using a cryogenic solid, a cryogenic gas, a cryogenic liquid or a heat transfer fluid capable of reaching cryogenic temperatures.

3. The method according to claim 1 wherein the freezable organic solvent is selected from the group consisting of alcohols, ethers, halocarbons, hydrocarbons, halogenated hydrocarbons, aromatic hydrocarbons, esters, acetates, organic acids, amines, ketones, sulfones, nitriles, carbonates, and combinations thereof.

4. The method according to claim 1 wherein the mean volume average particle size of the particles after the particles are dispersed in water is from 0.05 microns to 150 microns.

5. The method according to claim 1 wherein the solution further comprises at least one stabilizer.

6. The method according to claim 5 wherein the stabilizer is selected from the group consisting of phospholipids, surfactants, polymeric surfactants, vesicles, polymers selected from copolymers, homopolymers and block polymers, dispersion aids, and combinations thereof.

7. The method according to claim 1 wherein step (b) is performed using sublimation or evaporation.

* * * * *